United States Patent [19]

Trouyez

[11] Patent Number: 4,480,043

[45] Date of Patent: Oct. 30, 1984

[54] PROCESS FOR THE PREPARATION OF TOXOPLASMAS FOR THE DIAGNOSIS OF TOXOPLASMOSIS, AND PREPARATIONS THUS OBTAINED

[75] Inventor: Gérard Trouyez, Charbonnieres les Bains, France

[73] Assignee: Biomerieux, Charbonnieres les Bains, France

[21] Appl. No.: 262,893

[22] Filed: May 12, 1981

[30] Foreign Application Priority Data

May 20, 1980 [FR] France ............................. 80 11261

[51] Int. Cl.$^3$ ................... A61K 39/00; A61K 45/02; G01N 33/54; G01N 31/00
[52] U.S. Cl. ................................. 436/536; 436/543; 436/811; 435/7; 435/947; 424/85; 424/88
[58] Field of Search ................... 424/8, 12, 85, 87, 88, 424/92, 93; 435/4, 7, 29, 34, 947; 436/513, 519, 536, 811

[56] References Cited

PUBLICATIONS

Ardoin et al., CR Soc de Biol., (Paris), vol. 160, Oct. 1966, pp. 1821–1823.
Ardoin et al., CR Soc de Biol., (Paris), vol. 161, Jan 1967, pp. 117–119.
Fulton, Lancet, ii, 1959, pp. 1068–1069.
Novel, "Toxoplasmose: Vers une Clarification et une Synthese des Examens de Laboratoire", *Le Quotidien du Medeein*, vol. 2834, 1982, pp. 12–14.
Camargo, Inf and Immunity, vol. 21, Jul. 1978, pp. 55–58.
Shirahata, Chem. Abs., vol. 82, 1975, Ab. No. 29514z.

*Primary Examiner*—Albert T. Meyers
*Assistant Examiner*—K. S. McGowin
*Attorney, Agent, or Firm*—Brooks, Haidt, Haffner & Delahunty

[57] ABSTRACT

The invention relates to a process for obtaining preparations of toxoplasmas, improved for the diagnosis of toxoplasmosis by direct agglutination, said process comprising, in a first step, the inoculation in mice of a mixture of toxoplasmas and of sarcomatous cells, in a second step the inoculation in other mice of a mixture of sarcomatous cells infected with toxoplasmas coming from the mice of the first step and of non-infected sarcomatous cells, and finally the collection of the ascitic exsudate of these latter mice from 48 to 72 hours after inoculation.

9 Claims, No Drawings

PROCESS FOR THE PREPARATION OF TOXOPLASMAS FOR THE DIAGNOSIS OF TOXOPLASMOSIS, AND PREPARATIONS THUS OBTAINED

The present invention relates to a process for preparing toxoplasmas, i.e. suspensions of toxoplasmas intended for the diagnosis of toxoplasmosis by direct agglutination.

The diagnosis of acute infection with Gondii toxoplasmas depends on the results of the serological test. The number of problems connected with the available methods of serodiagnosis of this infection has been a stimulant for seeking other methods. At present, current methods available in practice to biologists are expensive to carry out, are long and are insufficiently sensitive to be useful at the first stage of the infection (cf. haemagglutination test).

The method proposed makes it possible both to obtain large quantities of antigens of toxoplasmas and considerably to improve the accuracy and sensitivity of the agglutination test, in particular by eliminating the non-specific agglutinations. Methods currently used up to the present time use whole, dead organisms. However, these methods, which are very simple, have two unfavourable characteristics:

Firstly, they lack sensitivity. In the agglutination test, the titer is generally much lower than in the lysis test or in the conventional immunofluorescence test. Consequently, some serums which may be positive in the latter two tests are in fact presented as negative by the agglutination method.

On the other hand, they lack specificity. A few serums, which are negative in the lysis and immunofluorescence tests give a positive result in the agglutination test.

The invention proposes to provide a method relative to the preparation of an antigen which increases the sensitivity of the agglutination test, and eliminates the non-specific agglutinations. The agglutination test thus modified enables results to be obtained which are equivalent to those obtained by the lysis tests.

The technique and reading of the new method proposed are so simple and precise that the availability of such an antigen will render considerable services to laboratories practising serology, whether it be occasionally or on a much larger scale.

It is an object of the invention to provide an improvement in the process for preparing an antigen resulting from the culture of toxoplasmas by simultaneous injection in mice, by the intraperitoneal route, of toxoplasmas and of sarcomatous cells, such as the cells of sarcoma TG 180. The process according to the invention makes it possible to obtain a considerable number of toxoplasmas per mouse, equivalent to about ten times what could be obtained by the conventional methods, according to which only the toxoplasma was inoculated in the mice.

The mice inoculated with a mixture of sarcomatous cells and of parasites, develop an exudate containing both sarcomatous cells and parasites, of which the proportion varies both as a function of the ratio of the parasites to the sarcomatous cells inoculated and of the time lapsed after inoculation. An examination of these exsudates under a microscope enables six stages to be distinguished.

In a first stage, the majority of the cells are not infected, and the few cells infected contain only few parasites.

In a second stage, 5 to 10% of the cells are infected, but each contains only few parasites.

In a third stage, about half the cells are infected, the majority containing only few parasites. A limited number of cells is very strongly infected. There are few extra-cellular toxoplasmas.

In a fourth stage, almost all the cells are broadly infected and close to bursting. Numerous extra-cellular parasites are found, but a negligible number if they are compared with the abundant intracellular organisms.

In a fifth stage, a large number of broadly infected cells is still found, close to bursting. At the same time, a large number of free toxoplasmas may be observed whose morphology appears normal.

Finally, in a sixth stage, all the sacromatous cells have been dislocated. There is a very large number of free parasites. Many organisms are manifestly dead or agglutinated.

The following two points must imperatively be respected for obtaining an antigen satisfactory for the agglutination test and for the immunofluorescence or staining tests: the exudates must be collected exclusively at the fourth and fifth stages; the mice must be inoculated less than 72 hours before thie exudate is collected, the optimal time being 48 hours. These two conditions are difficult to fulfill if the mice are inoculated with non-infected sarcomatous cells, mixed with toxoplasmas obtained from mice which have been inoculated with parasites alone. This is the reason why a two-step process has been developed.

The RH strain of toxoplasmas is conserved by successive intraperitoneal transfers from mouse to mouse, every two or three days. The sarcomatous cells for their part are the subject of intraperitoneal transfers on mice every 10 to 12 days.

The preparation of the antigen according to the invention involves two types of transfers.

Firstly, in a first step, the mice are inoculated with a mixture of toxoplasmas and of sarcomatous cells. For example, 2 ml of an exudate of sarcomatous cells advancing for 10 to 12 days are mixed with all the ascitic liquid of a mouse inoculated two to three days beforehand with the RH strain of toxoplasmas. This mixture is then centrifuged and the sediment is inoculated in mice by the intra-peritoneal route. Two days later, the exudate is examined under a microscope to check the absence of bacteria and the state of infection of the sarcomatous cells.

In a second step, the cells obtained during the first transfer are mixed with an adequate number of non-infected sarcomatous cells. To this end, on the one hand the exudate of the mice inoculated during the first transfer (containing the infected cells) is centrifuged and on the other hand the exudate of mice in which only sarcomatous cells (containing non-infected cells) have been inoculated, is centrifuged and the sedimented cells are mixed.

The optical ratio of the non-infected cells to the infected cells in the mixture varies as a function of the stage of infection of the mice of the first transfer, as shown in Table I below.

A certain volume, for example 2/10 ml of the appropriate mixture of non-infected and infected cells are then inoculated by the intra-peritoneal route to new mice. Two days later, the peritoneal exsudate will normally have attained the fourth and fifth stages, being then ready to be collected for the preparation of the antigen.

The following step consists in releasing, by action of trypsin or an equivalent, the toxoplasmas from the infected sarcomatous cells. The strongly infected cells are easily destroyed by this treatment. If the period of exposure to trypsin is too long, or if the concentration of the enzyme is too high during this exposure, the toxoplasmas will have a lower value as antigen, although they conserve their morphology. This is why this process must be interrupted by centrifugation and rejection of the trypsin, as soon as the majority of the toxoplasmas have been released from the sarcomatous cells. Operation is therefore as follows:

The sediment coming from the exudate of the mice of the second stage (stages IV and V of infection) is placed in suspension in a phosphate buffered saline solution (pH 7.2) or "PBS", containing 0.05% of trypsin and incubated in a water bath at 37° C. with continual stirring. Aliquot parts are examined every five minutes and immediately the rupture of the cells is observed, the suspension is centrifuged.

The sediment is again placed in suspension in a PBS solution and centrifuged. After this second centrifugation, the parasites are placed in suspension in a 6% solution of formaldehyde, in PBS. The parasites are kept overnight in the formaldehyde solution. The following day (at least 16 hours after suspension), they are again centrifuged. The sediment is then washed several times in PBS, so as to remove the debris of cells and the formaldehyde. The parasites are then suspended in an alkaline buffer (pH 8.7) containing a preserver agent.

The concentration of formaldehyde is high. The parasites must conserve their normal crescent form. When fixation is insufficient, a less sensitive antigen is obtained.

When the suspension is checked under the microscope, it is generally observed to be almost entirely constituted by free parasites. When only few sarcomatous cells remain, they are eliminated by centrifugation. If there is some fibrinous and coagulated matter, it may be eliminated by filtration. The concentration of parasites is adapted to give optimal results during the test with serums recognized positive in the lysis test. The suspension is maintained at 4° C. The optimal dilution is determined by titration of the different solutions of the mother suspension, with respect to the WHO standard or with respect to a secondary standard related to the WHO standard. As a general rule, a maximum agglutination of +++ is obtained until a dilution of 1/4,000 of the WHO standard is had, which corresponds to a final concentration of 0.125 international unit (I.U.) per milliliter in the reaction dish. The ++,+ readings are obtained with dilutions of 1/8,000 and 1/16,000 (0.063 and 0.031 IU/ml). A doubtful or negative result is obtained with dilutions of 1/32,000 (0.016 IU/ml). The dilution of the suspension used as antigen is that for which the results are the most clear in this value scale. In the majority of cases, it contains approximately from 10,000 to 50,000 and preferably 20,000 organisms per microliter. This concentration of parasites is therefore generally less than those described previously.

With this antigen, the reaction of agglutination on the serums is conducted in microtitration plates in the presence of 2-mercapto-ethanol, or equivalent. The results are expressed in titer (inverse of the dilution) or in international units (with respect to the WHO standard). The antigen thus described may also be used in the absence of 2-mercapto-ethanol.

TABLE I

Optimum ratio of the infected cells to the non-infected cells for the second transfer

| Stage of infection | Volume of the infected cells (sediment non-diluted) | Volume of the non-infected cells (non-diluted sediment) |
|---|---|---|
| I | 1 | 1 |
| II | 1 | 2 |
| III | 1 | 4 |
| IV | 1 | 16 |

What is claimed is:

1. A process for manufacturing a preparation of antigens of toxoplasmas whereby mixtures of toxoplasmas and cells of sarcoma TG 180 are inoculated in mice by the intraperitoneal route to produce toxoplasmas in the ascitic liquid, and the toxoplasmas are collected in the ascitic liquid obtained, wherein the process is improved by carrying out the operation in two steps: in the first step inoculating into mice a mixture of ascitic liquid containing toxoplasmas and ascitic liquid containing the sarcomatous cells and collecting the peritoneal exudate in from 48 to 72 hours after the inoculation, and in the second step inoculating into the mice a mixture of non-infected sarcomatous cells and sarcomatous cells infected by toxoplasmas obtained by centrifuging the exudate of the first step, collecting the peritoneal exudate from 48 to 72 hours after inoculation, and thereafter reacting the collected exudate with trypsin to free toxoplasmas from the cells.

2. The process of claim 1, wherein, in the first step, mice are inoculated with a mixture of ascitic liquid of a mouse inoculated two or three days beforehand by toxoplasmas, and of ascitic liquid of mice inoculated 10 to 12 days beforehand with sarcomatous cells, and the exudate of the mice inoculated with the mixture is collected from forty eight to seventy two hours after inoculation.

3. The process of claims 1 or 2, wherein, in the second step, the ratio of the number of infected sarcomatous cells to that of the non-infected sarcomatous cells varies as a function of the stage of infection of the mice in the first step.

4. The process of claims 1 or 2, wherein the sediment of the exudate collected during the second step is exposed in a water bath at 37° C. to the action of a 0.5% solution of trypsin in a buffered saline solution at pH 7.2, for just the time necessary to obtain rupture of the cells, releasing the toxoplasma.

5. The process of claim 4, wherein the released toxoplasmas are, after sedimentation, replaced in suspension in a 6% solution of formaldehyde, for at least 6 hours, then centrifuged, washed and placed in suspension in an alkaline buffer at pH 8.7 containing a preserver agent.

6. The process of claim 5, wherein the optimal concentration of the toxoplasmas in the alkaline buffer is determined by reference to an international standard, and is 10,000 to 50,000 toxoplasmas per liter.

7. In a process for diagnosis of toxoplasmosis by the direct agglutination test, the improvement comprising utilizing the antigen preparation of claim 1 as the reagent.

8. The process of claim 7, wherein the antigen preparation of claim 1 is carried out in the presence of 2-mercaptoethanol.

9. The process of claim 7, wherein the agglutination reaction on the serum to be tested is carried out on microtitration plates.

* * * * *

UNITED STATES PATENT AND TRADEMARK OFFICE
CERTIFICATE OF CORRECTION

PATENT NO. : 4,480,043

DATED : October 30, 1984

INVENTOR(S) : GERARD TROUYEZ

It is certified that error appears in the above-identified patent and that said Letters Patent is hereby corrected as shown below:

Column 2, line 18, "sacromatous" should read --sarcomatous--.

Column 2, line 27, "thie" should read --this--.

Column 2, line 61, "optical" should read --optimal--.

Claim 4, line 3, "0.5%" should read --0.05%--.

Signed and Sealed this

Twenty-eighth Day of May 1985

[SEAL]

Attest:

DONALD J. QUIGG

*Attesting Officer*  *Acting Commissioner of Patents and Trademarks*